(12) United States Patent
Dell et al.

(10) Patent No.: US 6,972,336 B2
(45) Date of Patent: *Dec. 6, 2005

(54) N-ALKYLATION OF INDOLE DERIVATIVES

(75) Inventors: Steven Dell, Madison, NJ (US); Mario Emilov Lozanov, Parsippany, NJ (US); Wen-Chung Shieh, Berkeley Heights, NJ (US)

(73) Assignee: Novartis AG, Basel (CH)

( * ) Notice: Subject to any disclaimer, the term of this patent is extended or adjusted under 35 U.S.C. 154(b) by 70 days.

This patent is subject to a terminal disclaimer.

(21) Appl. No.: 10/620,625

(22) Filed: Jul. 16, 2003

(65) Prior Publication Data

US 2004/0059131 A1 Mar. 25, 2004

Related U.S. Application Data

(60) Provisional application No. 60/396,827, filed on Jul. 18, 2002.

(51) Int. Cl.$^7$ ............................................. C07D 209/12
(52) U.S. Cl. ....................................................... 548/502
(58) Field of Search .......................................... 548/502

(56) References Cited

U.S. PATENT DOCUMENTS 6,326,501 B1 * 12/2001 Jiang ........................... 548/469
6,596,877 B2 * 7/2003 Shieh et al. ............. 548/343.5
6,706,929 B2    3/2004 Shieh et al.

FOREIGN PATENT DOCUMENTS

WO    01/81305    11/2001

OTHER PUBLICATIONS

Bergman et al., "Alkylation with Oxalic Esters. Scope and Mechanism", Tetrahedron, vol. 46, No. 17, pp. 6113–6124 (1990).
Ottoni et al., "Efficient and Simple Methods for the Introduction of the Sulfonyl, Acyl and Alkyl Protecting Groups on the Nitrogen of Indole and its Derivatives", Tetrahedron, vol. 54, pp. 13915–13928 (1998).
Shieh et al., "1,8–Diazabicyclo[5.4.0.]undec–7–ene (DBU) and Microwave–Accelerated Green Chemistry in Methylation of Phenols, Indoles, and Benzimidazoles with Dimethyl Carbonate", Organic Letters, vol. 3, No. 26, pp. 4279–4281 (2001).
Shieh et al., "Dual Nucleophilic Catalysis with DABCO for the N–Methylation of Indoles", J. Org. Chem., vol. 68, pp. 1954–1957 (2003).

Shieh et al., "Accelerated Benzylation Reaction Utilizing Dibenzyl Carbonate as an Alkylating Reagent", Tetrahedron Letters, vol. 44, pp. 6943–6945 (2003).
Tratrat et al., "Oxidative Cleavage of Indole δ–Lactones with m–Chloroperbenzoic Acid: First Synthesis of Spiroindolin–2–one γ–Lactones", J. Org. Chem., vol. 65, pp. 6773–6776 (2000).
Hilton et al., "A Tandem Radical Approach to the ABCE–R-ings of the Aspidosperma and Strychnos Alkaloida", Chem. Commun., pp. 209–210 (2001).

* cited by examiner

Primary Examiner—Kamal Saeed
(74) Attorney, Agent, or Firm—John W. Kung

(57) ABSTRACT

The present invention provides methods for the efficient preparation of indole derivatives of the formula

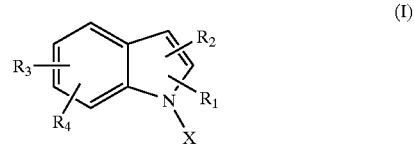

(I)

wherein X is methyl or benzyl; and $R_1$, $R_2$, $R_3$ and $R_4$ are independently hydrogen, halogen, cyano, nitro, hydroxy, optionally substituted alkyl, alkoxy, aralkoxy, carboxy, alkoxycarbonyl, aryl or heteroaryl; or $R_1$ and $R_2$ combined together with the carbon atoms to which they are attached form a fused 6-membered aromatic ring; by reacting indoles of the formula

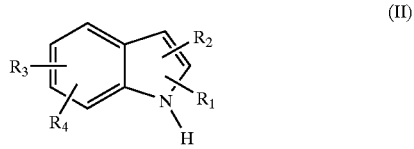

(II)

wherein $R_1$, $R_2$, $R_3$ and $R_4$ have meanings as defined for formula I, with dimethyl carbonate when X is methyl, or with dibenzyl carbonate when X is benzyl, in the presence of a catalytic amount of a base at an ambient temperature to afford compounds of formula I wherein X, $R_1$, $R_2$, $R_3$ and $R_4$ have meanings as defined herein above. In particular, the present invention provides methylation and benzylation of the indole nitrogen in nearly quantitative yields using 1,4-diazabicyclo[2.2.2]octane as the base in a catalytic amount under mild conditions, wherein the alkylations may be conducted in the absence or the presence of an ionic liquid, under microwave irradiation or utilizing conventional heat, or combinations thereof.

11 Claims, No Drawings

N-ALKYLATION OF INDOLE DERIVATIVES

This application claims the benefit of U.S. Provisional Application No. 60/396,827, filed Jul. 18, 2002.

BACKGROUND OF THE INVENTION

1. Field of the Invention

The present invention provides highly efficient, catalytic methods for N-alkylation of indole derivatives, more specifically the method provides N-methylindole and N-benzylindole derivatives.

2. Description of Related Art

N-Methylindole derivatives, such as indole alkaloids, are important natural products that exhibit a wide array of biological activities. For example, affinisine has been shown to produce delayed intention tremors, marked central nervous system (CNS) depressant activity, ataxia, hypothermia and bradypnea (Liu et al., *Tetrahedron Lett.*, 2000, 41, 6299), and a synthetic pentacyclic indole analog has revealed antitumoral properties (Christophe et al., *Tetrahedron Lett.* 1998, 39, 9431).

Common approaches to the synthesis of N-alkylindole derivatives typically require a two-step protocol: (1) formation of an active indole anion by stoichiometric amount of a strong base; and (2) reaction of the resulting anion with a toxic and hazardous alkylating agent such as methyl iodide, dimethyl sulfate, benzyl chloride or benzyl bromide (e.g. Hilton et al., *J. Chem. Soc., Chem. Commun.* 2001, 209; Tratrat et al., *J. Org. Chem.* 2000, 65, 6773; and Ottoni et al., *Tetrahedron* 1998, 54, 13915). Improved processes have been recently published utilizing non-toxic reagents, however, under harsh and stoichiometric conditions (Bergman et al., *Tetrahedron* 1990, 46, 6113). It has been reported that dimethyl carbonate may be employed effectively under milder conditions to N-methylate indole derivatives, however, these methods still demand the use of a stoichiometric amount of a base to achieve reasonable process efficiency (Shieh et al., *Organic Lett.* 2001, 3, 4279; and PCT Application No. WO 01/81305). Thus, development of an efficient, safe, and ecologically friendly methods for alkylation of indoles still constitutes an important challenge.

SUMMARY OF THE INVENTION

The present invention provides methods for the efficient preparation of indole derivatives of the formula

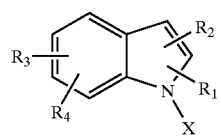

(I)

wherein X is methyl (Me) or benzyl (Bn), and $R_1$, $R_2$, $R_3$ and $R_4$ are independently hydrogen, halogen, cyano, nitro, hydroxy, optionally substituted alkyl, alkoxy, aralkoxy, carboxy, alkoxycarbonyl, aryl or heteroaryl; or $R_1$ and $R_2$ combined together with the carbon atoms to which they are attached form a fused 6-membered aromatic ring; by reacting indoles of the formula

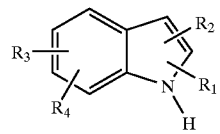

(II)

wherein $R_1$, $R_2$, $R_3$ and $R_4$ have meanings as defined for formula I, with dimethyl carbonate (DMC) when X is methyl, or with dibenzyl carbonate (DBC) when X is benzyl, in the presence of a catalytic amount of a base at an ambient temperature to afford compounds of formula I wherein X, $R_1$, $R_2$, $R_3$ and $R_4$ have meanings as defined herein above.

In particular, the present invention provides methylation and benzylation of the indole nitrogen in nearly quantitative yields using 1,4-diazabicyclo[2.2.2]octane (DABCO) as the base in a catalytic amount under mild conditions, wherein the alkylations may be conducted in the absence or the presence of an ionic liquid, under microwave irradiation or utilizing conventional heat, or combinations thereof.

Other objects, features, advantages and aspects of the present invention will become apparent to those skilled in the art from the following description and appended claims. It should be understood, however, that the following description, appended claims, and specific examples, while indicating preferred embodiments of the invention, are given by way of illustration only. Various changes and modifications within the spirit and scope of the disclosed invention will become readily apparent to those skilled in the art from reading the following.

DETAILED DESCRIPTION OF THE INVENTION

As described above, the present invention provides highly efficient, catalytic processes for the manufacture of N-methylindole and N-benzylindole derivatives.

Listed below are definitions of various terms used to describe the compounds of the instant invention. These definitions apply to the terms as they are used throughout the specification unless they are otherwise limited in specific instances either individually or as part of a larger group.

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkanoyloxy, amino, alkylamino, dialkylamino, thiol, alkylthio, alkylthiono, alkylsulfonyl, nitro, cyano, carboxy, alkoxycarbonyl, aryl, alkenyl, alkynyl, aralkoxy and the like.

The term "alkenyl" refers to any of the above alkyl groups having at least two carbon atoms and further containing a carbon to carbon double bond at the point of attachment. Groups having two to four carbon atoms are preferred.

The term "alkynyl" refers to any of the above alkyl groups having at least two carbon atoms and further containing a carbon to carbon triple bond double bond at the point of attachment. Groups having two to four carbon atoms are preferred.

The term "cycloalkyl" refers to optionally substituted monocyclic hydrocarbon groups of 3 to 7 carbon atoms, each of which may be substituted by one or more substituents such as alkyl, halo, oxo, hydroxy, alkoxy, alkylthio, nitro, cyano and the like.

Exemplary monocyclic hydrocarbon groups include but are not limited to cyclopropyl, cyclobutyl, cyclopentyl, cyclopentenyl, cyclohexyl and cyclohexenyl and the like.

The term "halogen" or "halo" refers to fluorine, chlorine, bromine and iodine.

The term "alkoxy" refers to alkyl-O—.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkylthio" refers to alkyl-S—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents such as alkyl, halo, hydroxy, alkoxy, alkylthio, nitro, cyano and the like.

The term "monocyclic aryl" refers to optionally substituted phenyl as described under aryl.

The term "aralkyl" refers to an aryl group bonded directly through an alkyl group, such as benzyl and phenethyl.

The term "aralkoxy" refers to an aryl group bonded directly through an alkoxy group.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g. lower alkyl, lower alkoxy or halo.

The term "ionic liquid" refers to organic salts that are liquid at or close to room temperature. They differ from common salts by having unusually low melting points. Ionic liquids tend to be liquid over a wide temperature range, they may be immiscible with a number of organic solvents as well as water, depending on the anion, and they may be employed as highly polar yet noncoordinating solvents. Furthermore, ionic liquids are nonvolatile and have essentially no vapor pressure. Most are air and water stable. The properties of the ionic liquids can be tailored by varying the cation and anion, the most common are those with alkylammonium, alkylphosphonium, N-alkylpyridinium and N,N-dialkylimidazolium cations.

Many ionic liquids are formed by reacting a tertiary amine or a nitrogen-containing heterocyclic ring, preferably a heteroaromatic ring, with an alkylating agent (e.g. an alkyl halide) to form a quaternary ammonium salt, and performing ion exchange or other suitable reactions with various Lewis acids or their conjugate bases to form ionic liquids. Examples of suitable tertiary amines and heteroaromatic rings include tri-n-butylamine, trioctylamine, trioctadecylamine, substituted pyridines, optionally substituted imidazoles and pyrroles. These compounds may be alkylated with virtually any straight, branched or cyclic $C_{1-20}$ alkyl group, but preferably, the alkyl groups are $C_{1-16}$ groups, since groups larger than this tend to produce low melting solids rather than ionic liquids.

Counterions which have been used include chloride, bromide, iodide, chloroaluminate, bromoaluminate, tetrafluoroborate, tetrachloroborate, hexafluoro-phosphate, nitrate, trifluoromethanesulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal containing anions.

Certain low melting solids may also be used in place of ionic liquids. Low melting solids are generally similar to ionic liquids but have melting points between room temperature and about 80° C., or they are liquids under the reaction conditions.

Examples of ionic liquids as defined herein above are tetra-n-butylammonium chloride (TBAC), tetra-n-butylammonium triflate (n-Bu$_4$N$^+$OTf$^-$), tetra-n-butylammonium tetrafluoroborate (n-Bu$_4$N$^+$BF$_4^-$), tetra-n-butylammonium hexafluorophosphate (n-Bu$_4$N$^+$PF$_6^-$), 1-n-butyl-3-methyl-imidazolium chloride (bmim$^+$Cl$^-$), 1-ethyl-3-methylimidazolium chloride (emim$^+$Cl$^-$) and 1-n-hexyl-3-methyl-imidazolium chloride (hmim$^+$Cl$^-$). Further examples of ionic liquids are described, e.g., in *J. Chem. Tech. Biotechnol*, 1997, 68, 351; *Chem. Ind.*, 1996, 68, 249; *J. Phys. Condensed Matter*, 1993, 5 (supp 34B), B99; *J. Mater. Chem.*, 1998, 8, 2627; and *Chem. Rev.*, 1999, 99, 2071.

The term "microwave irradiation" as used herein refers to microwave region of the electromagnetic spectrum corresponding to wavelengths from 1 cm to 1 m and to frequencies from 300 MHz to 30 GHz. By International Convention, however, domestic and industrial microwave ovens generally operate at greater than 900 MHz, preferably from about 2450 MHz to about 2455 MHz, in order to prevent interference with RADAR transmissions and telecommunications. Thus, the entire microwave region is not readily available for heating applications. Sources of microwave irradiation include multimode ovens and monomode ovens which may be batch or continuous devices. A preferred monomode oven is a continuous-flow reactor, such as a Milestone ETHOS-CFR continuous-flow reactor.

The methods of the present invention provides efficient catalytic processes for the preparation indole derivatives of the formula

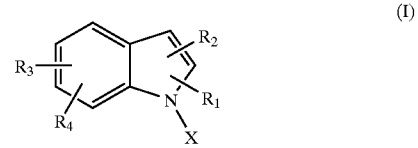

(I)

wherein X is methyl or benzyl, and $R_1$, $R_2$, $R_3$ and $R_4$ are independently hydrogen, halogen, cyano, nitro, hydroxy, optionally substituted alkyl, alkoxy, aralkoxy, carboxy, alkoxycarbonyl, aryl or heteroaryl; or $R_1$ and $R_2$ combined together with the carbon atoms to which they are attached form a fused 6-membered aromatic ring; by reacting indoles of the formula

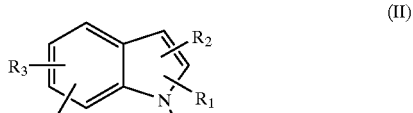

(II)

wherein $R_1$, $R_2$, $R_3$ and $R_4$ have meanings as defined for formula I, with DMC when X is methyl, or with DBC when X is benzyl, in the presence of a catalytic amount of a base, preferably DABCO, at an ambient temperature, preferably at a temperature ranging from about 80° C. to about 100° C. for N-methylation reactions, and from about 90° C. to about 150° C. for N-benzylation reactions, to afford compounds of formula I wherein X, $R_1$, $R_2$, $R_3$ and $R_4$ have meanings as defined herein above. More preferably, N-methylation reactions are carried out at a temperature ranging from about 90° C. to about 95° C., and N-benzylation reactions at a temperature of about 135° C. The reaction time may range from about 1 h to about 36 h for N-methylation, and from about 1 h to about 100 h for N-benzylation.

According to the methods of the present invention, alkylation of the indole nitrogen of compounds of formula II, wherein $R_1$, $R_2$, $R_3$ and $R_4$ have meanings as defined herein above, may be conducted in the presence or the absence of an organic solvent such as toluene, acetonitrile, N,N-dimethylformamide (DMF), N,N-dimethylacetamide (DMA) or N-methylpyrrolidinone (NMP), preferably DMF or DMA.

Alternatively, the alkylation reactions of the present invention may be carried out in the presence of an ionic liquid, preferably, TBAC. The ionic liquid may be employed as the reaction solvent, or it may be used as an additive when the alkylations are conducted in an organic solvent, such as those described herein above, to enhance the reaction rates. Preferably, the alkylations, in particular, the N-benzylation reactions are carried out in DMA in the presence of about one molar equivalent (equiv) of an ionic liquid.

In addition, microwave irradiation may be employed to enhance the rates of the alkylation reactions of the present invention. The alkylation reactions may be conducted under microwave irradiation at a frequency ranging from 300 MHz to 30 GHz generating a reaction temperature which ranges from about 120° C. to about 300° C., preferably, from about 140° C. to about 250° C. Most preferably, the alkylations are conducted at a temperature of about 160° C. Preferably, the alkylations are carried out for a period of microwave irradiation time ranging from about 1 second to about 300 min, more preferably from about 5 min to about 30 min. When the alkylations are carried out at a temperature greater than the boiling point of any of the components of the reaction mixture it may be advantageous to apply higher pressure in order to prevent boiling of either the reactants or the solvent. Generally, the microwave alkylations are conducted under a pressure ranging from about 1 bar to about 60 bar, preferably, from about 10 bar to about 35 bar, most preferably about 20 bar.

Preferably, the N-alkylation of indoles of formula II, wherein $R_1$, $R_2$, $R_3$ and $R_4$ have meanings as defined herein above, is carried out in a molar concentration (M) of the substrate ranging from 0.1 M to 1.0 M.

The molar ratio of the base to the substrate of formula II initially present in the reaction mixture ranges preferably from 0.01:1 to 0.5:1. More preferably, the molar ratio ranges from 0.05:1 to 0.15:1 for N-methylation reactions, and from 0.05:1 to 0.35:1 for N-benzylation reactions.

The effectiveness of DABCO as the base in the catalytic alkylation of the indole nitrogen of compounds of formula II, wherein $R_1$, $R_2$, $R_3$ and $R_4$ have meanings as defined herein above, using DMC or DBC as the alkylating agent under mild reaction conditions may be demonstrated with 5-bromoindole of formula IIa. As illustrated in the Table 1 below, in the presence of 0.1 equiv (10 mol %) of DABCO, the catalytic process described herein above affords N-methylindole of formula Ia (X is methyl, entry 5) quantitatively within 5 h when heated at 90° C.

TABLE 1

N-Alkylation of 5-bromoindole.[a]

| Entry | X | Time (h) | Base | % of IIa | % of Ia | % of III |
|---|---|---|---|---|---|---|
| 1[b] | Me | 5 | None | 100 | 0 | 0 |
| 2[b] | Me | 5 | n-Bu$_3$N | 100 | 0 | 0 |
| 3[b] | Me | 5 | DMAP | 14 | 12 | 73 |
| 4[b] | Me | 5 | DBU | 9 | 6 | 84 |
| 5[b] | Me | 5 | DABCO | 0 | >99 | 0 |
| 6[c] | Bn | 96 | None | 84 | 5 | 11 |
| 7[c] | Bn | 96 | DABCO | 20 | 80 | 0 |
| 8[d] | Bn | 24 | None | 53 | 43 | 4 |
| 9[d] | Bn | 24 | DABCO | 12 | 82 | 6 |

[a]All reactions are conducted using 0.1 equiv of the base if not otherwise indicated. The compound distributions are determined by HPLC analysis of the reaction mixture. The identity of the components is confirmed by $^1$H NMR, $^{13}$C NMR and MS.
[b]The reaction is conducted on 5 mmol scale in 1 mL of DMF and 10 mL of DMC at 90° C.
[c]The reaction is conducted on 2 mmol scale in 4 mL of DMA and 3 mmol of DBC at 95° C.
[d]The reaction is conducted on 2 mmol scale in 4 mL of DMA and 3 mmol of DBC at 135° C.

In contrast thereto, the N-methylation using 0.1 equiv of N,N-dimethylamino-pyridine (DMAP) or 1,8-diazabicyclo [5.4.0]undec-7-ene (DBU) affords the methylcarbamate of formula III (X is methyl, entries 3 and 4) as the major component of the reaction mixture. It should be noted that without any base catalyst or in the presence of tri-n-butylamine (n-BU$_3$N), the N-methylation generates no product at all (entries 1 and 2). Similarly, the catalytic process of the present invention provides N-benzylindole of formula Ia (X is benzyl, entries 7 and 9) in good yield in the presence of only 0.1 equiv of DABCO. As the data in Table 1 illustrate, the N-benzylation reactions are generally slower than the corresponding N-methylations and require higher reaction temperatures and longer reaction times under the reaction conditions employed herein.

The effect of a variety of ionic liquids on the reaction rates of N-alkylation reactions of the present invention may be demonstrated with N-benzylation of indole derivative of formula IIb. As shown in Table 2, indole of formula IIb, i.e., carbazole, may be converted to N-benzylindole of formula Ib within 3 h in excellent yield in the presence of one equiv of TBAC (entry 9). In comparison, the imidazolium-series of ionic liquids are less effective, and ionic liquids that contain a chloride anion consistently perform better than the ones containing a different counterion (entries 5 and 7 to 9).

TABLE 2

The effect of ionic liquids on the benzylation rate of carbazole.[a]

| Entry | Ionic Liquid | % of Ib[b] |
|---|---|---|
| 1 | None[c] | 59 |
| 2 | bmim+ OTf | 28 |
| 3 | bmim+ BF4− | 34 |
| 4 | bmim+ PF6− | 28 |
| 5 | bmim+ Cl− | 65 |
| 6 | emim+ BF4− | 28 |
| 7 | emim+ Cl− | 66 |
| 8 | hmim+ Cl− | 79 |
| 9 | TBAC | 93 |

[a]All reactions, except entry 1, are conducted with 2 mmol of IIb, 3 mmol of DBC, 0.6 mmol of DABCO, and 2 mmol of an ionic liquid in 4 mL of DMA at 135° C. for 3 h.
[b]The yields are determined by HPLC analysis of the reaction mixture at the end of the reaction time indicated.
[c]Same as procedure a, except no ionic liquid is present.

The effect of an ionic liquid on the reaction rates of N-benzylation reactions according to the present invention is further illustrated in Table 3. In a typical experiment, a substrate (2 mmol), i.e., an indole of formula II, DABCO (10–30 mol %), DBC (3 mmol), TBAC (2 mmol) in DMA (4 mL) are heated at 135° C. and the reaction is monitored by HPLC until a trace or no starting material is detected. As promoted by TBAC, the benzylation rates for 5-bromoindole (IIa), carbazole (IIb) and the unsubstituted indole (IIc) are significantly improved as shown by impressive reductions in reaction times to 0.5 h (entry 1), 3 h (entry 2) and 2 h (entry 3), respectively. In the absence of TBAC, the same reactions take 24 h, 72 h and 45 h under otherwise identical reaction conditions.

TABLE 3

Reduction of reaction times of N-benzylation in the presence of n-Bu4N+Cl−.[a]

| Entry | Substrate | Product[a] | Thermal[b] (time, yield)[c] | Ionic Liquid[d] (time, yield)[c] | Microwave[g] (time, yield)[c] |
|---|---|---|---|---|---|
| 1[e] | IIa | Br-indole-Bn | 24 h, 79% | 0.5 h, 83% | 6 min, 76% |
| 2[f] | IIb | carbazole-Bn | 72 h, 80% | 3 h, 89% | 18 min, 82% |
| 3[f] | IIc | indole-Bn | 45 h, 82% | 2 h, 80% | 12 min, 70% |

[a]The identity of the benzylated products is confirmed by $^1$H and $^{13}$C NMR and MS.
[b]General procedure using conventional thermal heating: a reaction flask is charged with the substrate (2 mmol), DARCO (10–30 mol %), DMA (4 mL), and DBC (3 mmol). The mixture is heated at 135° C., and the reaction is monitored by HPLC until trace or no starting substrate is detected (reaction time).
[c]Isolated yield based on starting substrate.
[d]Same as procedure b, except 1 equiv of TBAC is added to the reaction mixture.
[e]10 mol % of DABCO.
[f]30 mol % of DABCO.
[g]Gereal procedure using microwave heating: A solution of the substrate (20 mmol), DBC (60 mmol), DABCO (10–30 mol %), TBAC (20 mmol) in CH$_3$CN (80 mL) is passed through a Milestone ETHOS-CFR continuous-flow reactor preheated to 160° C. at 20 bar. The reaction products are analyzed by HPLC after each pass (6 min).

It may be required to introduce protecting groups to protect other functional groups from undesired reactions with the reaction components under the conditions used for carrying out the N-alkylation of the indole nitrogen of compounds of formula II. The need and choice of protecting groups for a particular reaction is known to those skilled in the art and depends on the nature of the functional group to be protected, the structure and stability of the molecule of which the substituent is a part and the reaction conditions.

Well known protecting groups that meet these conditions and their introduction and removal are described, for example, in McOmie, "Protective Groups in Organic Chemistry", Plenum Press, London, N.Y., 1973; and Greene and Wuts, "Protective Groups in Organic Synthesis", John Wiley and Sons, Inc., NY, 1999.

The following Examples are intended to illustrate the invention and are not to be construed as being limitations thereon. If not mentioned otherwise, the processes described herein above are conducted under inert atmosphere, preferably under nitrogen atmosphere. All evaporations are performed under reduced pressure, preferably between about 5 and 100 mmHg. The structure of products and starting materials is confirmed by standard analytical methods, e.g. melting points (mp) and spectroscopic characteristics (e.g. MS, NMR). Abbreviations used are those conventional in the art.

EXAMPLE 1

5-Bromo-1-methylindole

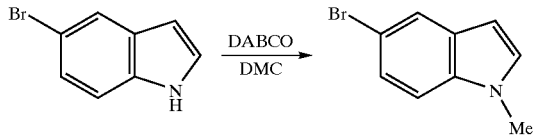

To a solution of 5-bromoindole (1.0 g, 5.10 mmol) in DMC (10 mL), DABCO (0.057 g, 0.51 mmol) is added followed by DMF (1 mL). The resulting solution is heated to 90–95° C. for 5 h. The reaction is cooled to RT, and diluted with ethyl acetate (EtOAc, 50 mL) and $H_2O$ (50 mL). The organic layer is separated and washed in sequence with $H_2O$ (50 mL), 10% aqueous citric acid (2×50 mL) and $H_2O$ (4×50 mL). The organic layer is dried over anhydrous sodium sulfate ($Na_2SO_4$), filtered and concentrated under vacuum to give 5-bromo-1-methylindole (about 1.06 g, 99%) as a golden colored solid: $^1$H NMR (CDCl$_3$) δ7.72 (d, 1H), 7.26 (dd, 1H), 7.13 (d, 1H), 7.00 (d, 1H), 6.39 (d, 1H), 3.71 (s, 3H); $^{13}$C NMR (CDCl$_3$) δ135.3, 130.1, 129.9, 124.2, 123.2, 112.6, 110.6, 100.5, 32.9; MS m/z 209 [M+1]$^+$.

EXAMPLE 2

5-Methoxy-1-methylindole

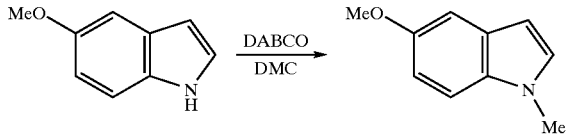

To a solution of 5-methoxyindole (1.0 g, 6.79 mmol) in DMC (10 mL), DABCO (0.076 g, 0.68 mmol) is added followed by DMF (2 mL). The resulting solution is heated to 90–95° C. for 7 h. The reaction is cooled to RT, and diluted with EtOAc (40 mL) and $H_2O$ (40 mL). The organic layer is separated and washed in sequence with $H_2O$ (50 mL), 10% aqueous citric acid (2×40 mL) and $H_2O$ (4×40 mL). The organic layer is dried over anhydrous $Na_2SO_4$, filtered and concentrated under vacuum to give 5-methoxy-1-methylindole (about 1.06 g, 97%) as a solid: $^1$H NMR (CDCl$_3$) δ7.21 (d, 1H), 7.09 (d, 1H), 7.00 (d, 1H), 6.87 (dd, 1H) 6.39 (d, 1H), 3.84 (s, 3H), 3.73 (s, 3H); $^{13}$C NMR (CDCl$_3$) δ153.9, 132.1, 129.3, 128.7, 111.8, 109.9, 102.4, 100.3, 55.9, 32.9; MS m/z 161 [M+1]$^+$.

EXAMPLE 3

3-Cyano-1-methylindole

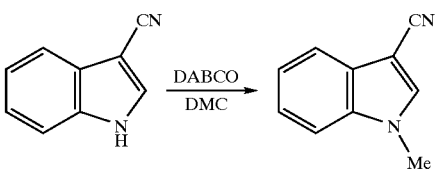

To a solution of 3-cyanoindole (1.0 g, 7.03 mmol) in DMC (10 mL), DABCO (0.079 g, 0.70 mmol) is added and the resulting solution is heated to reflux for 8 h. The reaction is cooled to RT, and diluted with EtOAc (40 mL) and $H_2O$ (40 mL). The organic layer is separated and washed in sequence with $H_2O$ (50 mL), 10% aqueous citric acid (2×40 mL) and $H_2O$ (4×40 mL). The organic layer is dried over anhydrous $Na_2SO_4$, filtered and concentrated under vacuum to give 3-cyano-1-methylindole (about 1.08 g, 98%) as an oil: $^1$H NMR (CDCl$_3$) δ7.74 (d, 1H), 7.53 (s, 1H), 7.40–7.28 (m, 3H), 3.83 (s, 3H); $^{13}$C NMR (CDCl$_3$) 136.0, 135.6, 127.8, 123.8, 122.1, 119.8, 116.0, 110.4, 85.4, 33.6; MS m/z 156 [M+1]$^+$.

EXAMPLE 4

1-Methylindole-2-carboxylate

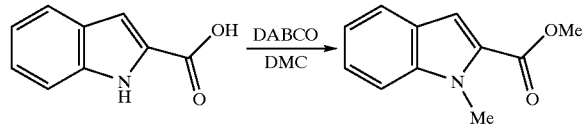

To a solution of indole-2-carboxylic acid (1.0 g, 6.21 mmol) in DMC (10 mL), DABCO (0.77 g, 6.83 mmol) is added followed by DMF (4 mL) and the resulting solution is heated to 90–95° C. for 21 h. The reaction is cooled to RT, and diluted with EtOAc (50 mL) and $H_2O$ (40 mL). The organic layer is separated and washed in sequence with $H_2O$ (50 mL), 10% aqueous citric acid (2×40 mL), saturated agueous sodium bicarbonate (NaHCO$_3$, 2×40 mL) and $H_2O$ (2×40 mL). The organic layer is dried over anhydrous $Na_2SO_4$, filtered and concentrated under vacuum to give 1-methylindole-2-carboxylate (about 1.12 g, 95%) as a solid: $^1$H NMR (CDCl$_3$) δ7.68 (d, 1H), 7.37–7.29 (m, 3H), 7.15 (app dt, 1H), 4.07 (s, 3H), 3.91 (s, 3H); $^{13}$C NMR (CDCl$_3$) δ162.6, 139.6, 127.6, 125.8, 125.0, 122.6, 120.5, 110.2, 110.22, 110.18, 51.6, 31.64; MS m/z 189 [M+1]$^+$.

EXAMPLE 5

9-Methylcarbazole

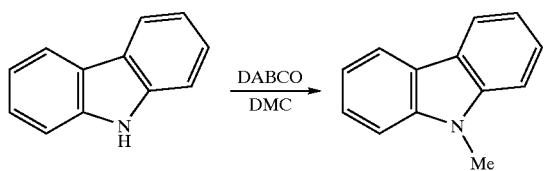

To a solution of carbazole (1.03 g, 6.16 mmol) in DMC (10 mL), DABCO (0.069 g, 0.62 mmol) is added and the resulting solution is heated to 90–95° C. for 24 h. The reaction is cooled to RT, and diluted with EtOAc (40 mL) and H$_2$O (40 mL). The organic layer is separated and washed in sequence with H$_2$O (50 mL), 10% aqueous citric acid (2×40 mL) and H$_2$O (3×40 mL). The organic layer is dried over anhydrous Na$_2$SO$_4$, filtered and concentrated under vacuum to give 9-methylcarbazole (about 1.08 g, 97%) as a beige solid: $^1$H NMR (CDCl$_3$) δ8.06 (d, 2H), 7.43 (t, 2H), 7.31 (d, 2H), 7.20 (t, 2H), 3.71 (s, 3H); $^{13}$C NMR (CDCl$_3$) δ141.0, 125.7, 122.8, 120.3, 118.9, 108.5, 29.0; MS m/z 181 [M+1]$^+$.

EXAMPLE 6

1-Methylindole

The title compound is prepared analogously to the previous Examples in about 97% yield: $^1$H NMR (CDCl$_3$) δ7.62 (d, 1H), 7.32 (d, 1H), 7.22 (t, 1H), 7.12 (t, 1H), 7.04 (d, 1H), 6.48 (d, 1H) 3.78 (s, 3H); $^{13}$C NMR (CDCl$_3$) δ136.7, 128.8, 128.5, 121.5, 120.9, 119.3, 109.2, 100.9, 32.8; MS m/z 131 [M+1]$^+$.

EXAMPLE 7

1-Methyl-5-nitroindole

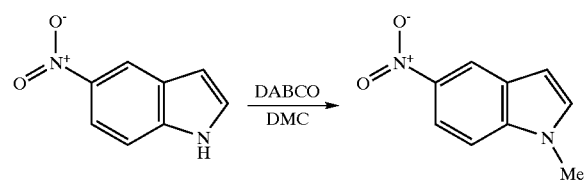

The title compound is prepared analogously to the previous Examples in about 95% yield: $^1$H NMR (CDCl$_3$) δ8.57 (d, 1H), 8.11 (dd, 1H), 7.33 (d, 1H), 7.21 (d, 1H), 6.67 (d, 1H), 3.86 (s, 3H); $^{13}$C NMR (CDCl$_3$) δ141.5, 139.4, 132.0, 127.6, 118.2, 117.2, 109.1, 103.8, 33.3; MS m/z 176 [M+1]$^+$.

EXAMPLE 8

1-Methyl-2-phenylindole

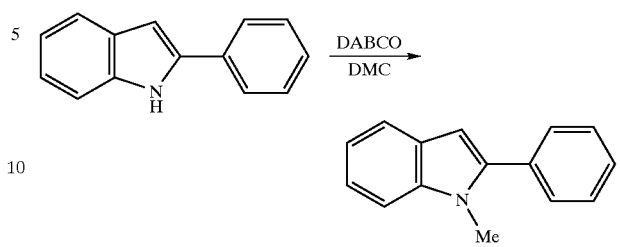

The title compound is prepared analogously to the previous Examples in about 97% yield: $^1$H NMR (CDCl$_3$) δ7.66 (d, 1H), 7.53–7.35 (m, 6H), 7.25 (dd, 1H), 7.14 (t, 1H), 6.57 (s, 1H), 3.75 (s, 3H); $^{13}$C NMR (CDCl$_3$) δ141.5, 138.3, 132.8, 129.3, 128.5, 127.9, 127.8, 121.6, 120.5, 119.8, 109.6, 101.6, 31.1; MS m/z 208 [M+1]$^+$.

EXAMPLE 9

1-Benzyl-5-bromoindole

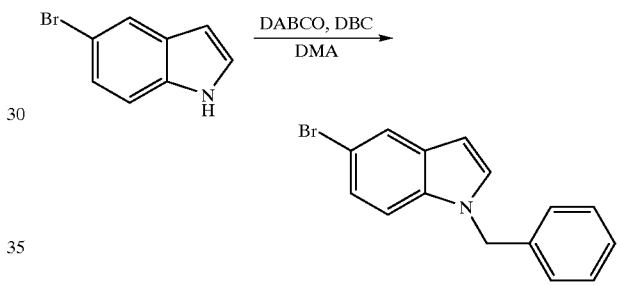

To a mixture of 5-bromoindole (392 mg, 2.0 mmol), DBC (726 mg, 3.0 mmol) and DABCO (22.4 mg, 0.2 mmol) is added DMA (4 mL). The resulting solution is heated at 135° C. for 24 h. The reaction mixture is cooled to RT and diluted with EtOAc (50 mL) and H$_2$O (50 mL). The two layers are separated and the aqueous layer is back extracted with EtOAc (50 mL). The combined organic layers are washed with brine and dried over anhydrous Na$_2$SO$_4$. The mixture is filtered and concentrated under vacuum. The crude residue is purified with Biotage Flash Chromatography unit on 40 s cartridge eluting with hexane:CH$_2$Cl$_2$=19:1 solvent mixture to afford 5-bromo-1-benzylindole (about 451.9 mg, 79%) as a white solid: mp 90° C.; $^1$H NMR (CDCl$_3$) δ7.68 (d, 1H), 7.16 (m, 4H), 7.04 (m, 4H), 6.40 (d, 1H), 5.20 (s, 2H); $^{13}$C NMR (CDCl$_3$) δ137.0, 134.9, 130.4, 129.4, 128.8, 127.7, 126.6, 124.5, 123.4, 112.8, 111.1, 101.2, 50.2; MS m/z 285.0150 [M+1]$^+$.

EXAMPLE 10

1-Benzyl-5-nitroindole

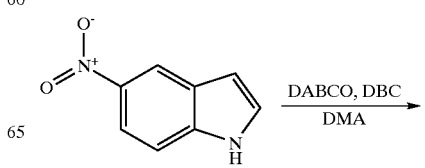

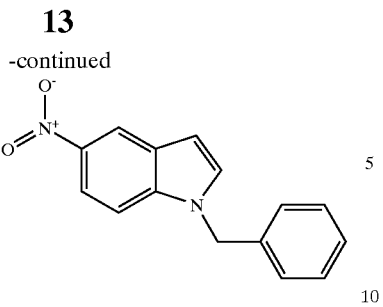

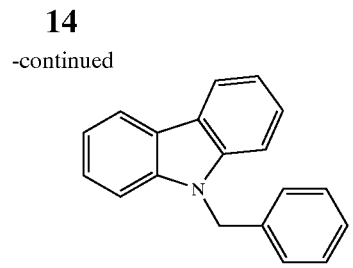

The title compound is prepared analogously to example 9 in about 90% yield as a white solid: mp 103° C.; $^1$H NMR (CDCl$_3$) δ8.45 (d, 1H), 7.91 (dd, 1H), 7.15 (m, 5H), 6.95 (m, 2H), 6.57 (d, 1H), 5.21 (s, 2H); $^{13}$C NMR (CDCl$_3$) δ141.7, 139.0, 136.1, 131.4, 129.0, 128.1, 127.9, 126.7, 118.2, 117.4, 109.6, 104.4, 50.6; MS m/z 252.0892 [M+1]$^+$.

EXAMPLE 11

1-Benzylindole

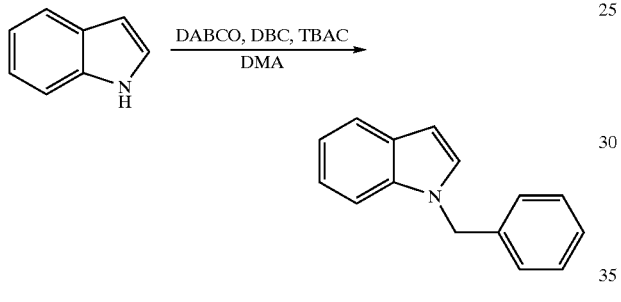

To a mixture of indole (234 mg, 2.0 mmol), DBC (726 mg, 3.0 mmol), DABCO (67.2 mg, 0.6 mmol) and TBAC (556 mg, 2.0 mmol) is added DMA (4 mL). The resulting solution is heated at 135° C. for 2 h. The reaction mixture is cooled to RT and diluted with EtOAc (50 mL) and H$_2$O (50 mL). The two layers are separated and the aqueous layer is back extracted with EtOAc (50 mL). The combined organic layers are washed with brine and dried over anhydrous Na$_2$SO$_4$. The mixture is filtered and concentrated under vacuum. The crude residue is purified with Biotage Flash Chromatography unit on 40 s cartridge eluting with hexane:CH$_2$Cl$_2$=19:1 solvent mixture to afford 1-benzylindole (about 331.2 mg, 80%) as a white solid: mp 43° C.; $^1$H NMR (CDCl$_3$) δ7.38 (m, 9H), 6.73 (d, 1H), 5.48 (s, 2H); $^{13}$C NMR (CDCl$_3$) δ137.5, 136.3, 128.7, 128.2, 127.6, 126.7, 121.6, 120.9, 119.5, 109.7, 101.6, 50.0; MS m/z 207.1043 [M+1]$^+$.

EXAMPLE 12

1-Benzylcarbazole

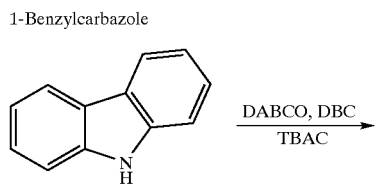

A mixture of carbazole (167 mg, 1.0 mmol), DBC (363 mg, 1.5 mmol), DABCO (33.6 mg, 0.3 mmol) and TBAC (2.0 g) is heated at 135° C. for 1 h. A small sample is taken from the melt, cooled down to RT, and added a mixture of H$_2$O (1 mL) and Et$_2$O (1 mL). The organic layer is separated and Et$_2$O is evaporated. The residue is dissolved into a mixture of H$_2$O:CH$_3$CN=1:1 (1 mL) and subjected to a HPLC analysis on Waters 717 HPLC instrument with Symmetry Shield RP$_8$ 3.9×150 mm column eluting with 50:50H$_2$O:CH$_3$CN solvent mixture at 40° C. Chromatogram indicated about 91% conversion to the desired product 1-benzylcarbazole.

EXAMPLE 13

1-Benzyl-5-bromoindole

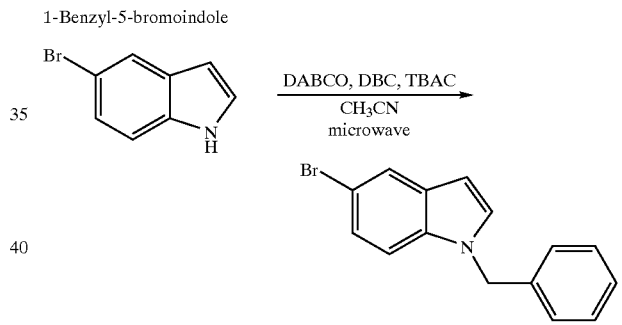

A mixture of 5-bromoindole (3.92 g, 20 mmol), DBC (14.52 g, 60 mmol), DABCO (224 mg, 2.0 mmol) and TBAC (5.56 g, 20 mmol) is dissolved in CH$_3$CN (80 mL). The resulting solution is subjected to microwave irradiation by passing through (flow rate=20 mL/min) a Milestone ETHOS-CFR continuous-flow reactor, which is preheated at 160° C. under 20 bar pressure. After the first pass (6 min) the reaction mixture is collected and cooled to ambient temperature. The mixture is concentrated under vacuum. The residue is diluted with EtOAc and H$_2$O. The two layers are separated and the aqueous layer is back extracted with EtOAc. The combined organic layers are washed with brine and dried over anhydrous Na$_2$SO$_4$. The mixture is filtered and concentrated under vacuum. The crude residue is purified with Biotage Flash Chromatography unit on 40 s cartridge eluting with hexane:CH$_2$Cl$_2$=19:1 solvent mixture to afford 5-bromo-1-benzylindole (about 76% yield) as a white solid: mp 90° C.; $^1$H NMR, $^{13}$C NMR and MS data match the ones reported in Example 9.

EXAMPLE 14

1-Benzyl-carbazole

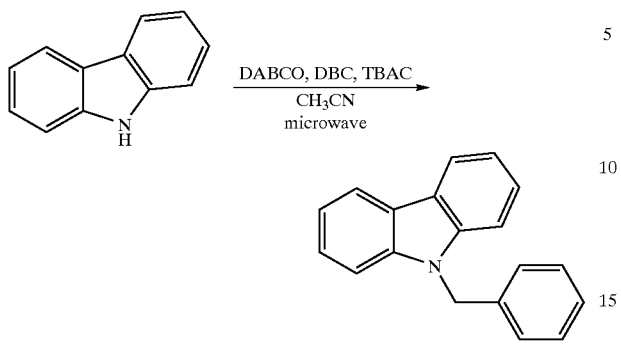

A mixture of carbazole (3.34 g, 20 mmol), DBC (14.52 g, 60 mmol), DABCO (672 mg, 6.0 mmol) and TBAC (5.56 g, 20 mmol) is dissolved in $CH_3CN$ (80 mL). The resulting solution is subjected to microwave irradiation by passing through (flow rate 20 mL/min) a Milestone ETHOS-CFR continuous flow reactor, which is preheated at 160° C. under 20 bar pressure. After the third pass (18 min), the reaction mixture is collected and cooled to RT. The mixture is concentrated under vacuum. The residue is diluted with EtOAc and $H_2O$. The two layers are separated and the aqueous layer is back extracted with EtOAc. The combined organic layers are washed with brine and dried over anhydrous $Na_2SO_4$. The mixture is filtered and concentrated under vacuum. The crude residue is purified with Biotage Flash Chromatography unit on 40 s cartridge eluting with hexane:$CH_2Cl_2$=19:1 solvent mixture and afforded 1-benzylcarbazole (about 76% yield) as a white solid: mp 117° C.; $^1H$ NMR ($CDCl_3$) δ8.05 (d, 2H), 7.20 (m, 11H), 5.42 (s, 2H); $^{13}C$ NMR ($CDCl_3$) δ140.6, 137.1, 128.7, 127.4, 126.4, 125.8, 123.0, 120.3, 119.1, 46.5; MS m/z 257.1202 $[m+1]^+$.

What is claimed is:

1. A method for the preparation of indole derivatives of the formula

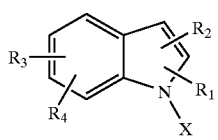
(I)

wherein X is methyl; and $R_1$ and $R_2$ are independently hydrogen or optionally substituted alkyl, $R_3$ is halogen; and $R_4$ is hydrogen, halogen, cyano, nitro, hydroxyl, optionally substituted alkyl, alkoxy, aralkoxy, carboxy, alkoxycarbonyl, aryl, or heteroaryl; which method comprises reacting indoles of the formula

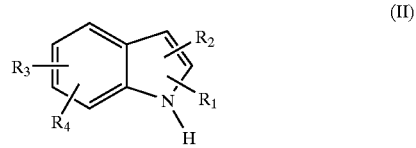
(II)

wherein $R_1$, $R_2$, $R_3$ and $R_4$ have meanings as defined for formula I;

with dimethyl carbonate when X is methyl;

in the presence of a catalytic amount of 1,4-diazabicyclo[2.2.2]octane at an ambient temperature.

2. The method according to claim 1, wherein the molar ratio of 1,4diazabicyclo[2.2.2]octane to the compound of formula II initially present in the reaction mixture ranges from 0.01:1 to 0.5:1.

3. The method according to claim 2, wherein the molar ratio of the base to the compound of formula II initially present in the reaction mixture ranges from 0.05:1 to 0.15:1.

4. The method according to claim 2, wherein the ambient temperature ranges from 80° C. to 100° C.

5. The method according to claim 2, wherein the reaction is carried out in the presence of an organic solvent.

6. The method according to claim 5, wherein the organic solvent is selected from the group consisting of toluene, acetonitrile, N,N-dimethylformamide, N,N-dimethylacetamide and N-methylpyrrolidinone.

7. The method according to claim 6, wherein the organic solvent is N,N-dimethyl-formamide.

8. The method according to claim 7, wherein the ambient temperature ranges from 90° C. to 95° C.

9. The method according to claim 2, wherein the reaction is carried out in the presence of an ionic liquid.

10. The method according to claim 9, wherein the ionic liquid is tetra-n-butylammonium chloride.

11. The method according to claim 2, wherein the reaction is conducted under microwave irradiation at a frequency from 300 MHz to 30 GHz, and at a temperature ranging from 80° C. to 300° C. for a period of microwave irradiation time ranging from 1 second to 300 min.

* * * * *